(12) United States Patent
Tearney et al.

(10) Patent No.: US 11,571,112 B2
(45) Date of Patent: Feb. 7, 2023

(54) METHOD AND APPARATUS FOR RECORDING MICROSCOPIC IMAGES FROM WITHIN A LIVING PERSON OR ORGANISM USING AN IMPLANTABLE DEVICE

(71) Applicant: The General Hospital Corporation, Boston, MA (US)

(72) Inventors: Guillermo J. Tearney, Cambridge, MA (US); Timothy N. Ford, Allston, MA (US); Robert Carruth, Arlington, MA (US); Tao Wu, Cambridge, MA (US); Chulho Hyun, Cambridge, MA (US); Weina Lu, Cambridge, MA (US); Kengyeh Ken Chu, Jamaica Plain, MA (US)

(73) Assignee: The General Hospital Corporation, Boston, MA (US)

( * ) Notice: Subject to any disclaimer, the term of this patent is extended or adjusted under 35 U.S.C. 154(b) by 11 days.

(21) Appl. No.: 15/110,380

(22) PCT Filed: Jan. 7, 2015

(86) PCT No.: PCT/US2015/010445
§ 371 (c)(1),
(2) Date: Jul. 7, 2016

(87) PCT Pub. No.: WO2015/105850
PCT Pub. Date: Jul. 16, 2015

(65) Prior Publication Data
US 2016/0331209 A1     Nov. 17, 2016

Related U.S. Application Data

(60) Provisional application No. 61/924,574, filed on Jan. 7, 2014.

(51) Int. Cl.
*A61B 1/00* (2006.01)
*A61B 1/04* (2006.01)
*A61B 5/00* (2006.01)

(52) U.S. Cl.
CPC ...... *A61B 1/00016* (2013.01); *A61B 1/00006* (2013.01); *A61B 1/00009* (2013.01);
(Continued)

(58) Field of Classification Search
CPC .................................................... A61B 1/041
(Continued)

(56) References Cited

U.S. PATENT DOCUMENTS

| 7,534,207 B2 * | 5/2009 | Shehada | A61B 5/0031 600/301 |
| 2003/0018280 A1 * | 1/2003 | Lewkowicz | A61B 1/00082 600/549 |

(Continued)

FOREIGN PATENT DOCUMENTS

WO    WO 2013/148360    10/2013

OTHER PUBLICATIONS

Michael W. Davidson, "Resolution", MicroscopyU, Nikon.*
(Continued)

*Primary Examiner* — Alexandra L Newton
(74) *Attorney, Agent, or Firm* — Quarles & Brady LLP

(57) ABSTRACT

Exemplary apparatus and method can be provided. For example, using at least one light source first arrangement, it is possible to provide pulses of light to at least one portion of a biological structure. At least one detector second arrangement can be used to detect images from the portion(s) based on the pulses, and provide data based on the detection. With at least one configuration, it is possible prevent and/or reduce a movement of the apparatus within at least one anatomical body (i) is a particular surface of the (Continued)

apparatus, (ii) covers at least one portion of the surface, and/or (iii) extends from the surface. In addition or alternatively, with at least one computer third arrangement, it is possible to receive the data, and control a timing of at least one of activation or deactivation of at least one portion of the first arrangement based on the data.

25 Claims, 20 Drawing Sheets

(52) U.S. Cl.
CPC ...... *A61B 1/00025* (2013.01); *A61B 1/00147* (2013.01); *A61B 1/00177* (2013.01); *A61B 1/041* (2013.01); *A61B 1/043* (2013.01); *A61B 5/0066* (2013.01)

(58) Field of Classification Search
USPC .......................................... 600/114
See application file for complete search history.

(56) References Cited

U.S. PATENT DOCUMENTS

| | | | |
|---|---|---|---|
| 2005/0004474 A1* | 1/2005 | Iddan | A61B 1/00158 600/476 |
| 2005/0259487 A1* | 11/2005 | Glukhovsky | A61B 1/04 365/202 |
| 2005/0261552 A1 | 11/2005 | Mori et al. | |
| 2006/0178557 A1 | 8/2006 | Mintchev et al. | |
| 2006/0210603 A1 | 9/2006 | Williams et al. | |
| 2008/0140341 A1 | 6/2008 | Ralston et al. | |
| 2008/0304128 A1 | 12/2008 | Busker et al. | |
| 2009/0093728 A1* | 4/2009 | Hyde | A61B 1/041 600/476 |
| 2009/0177033 A1 | 7/2009 | Hendriks et al. | |
| 2011/0001789 A1* | 1/2011 | Wilson | G02B 13/06 348/36 |
| 2011/0306897 A1 | 12/2011 | Imran | |
| 2012/0050888 A1* | 3/2012 | Dai | G02B 13/0035 359/716 |
| 2012/0071710 A1 | 3/2012 | Gazdzinski | |
| 2012/0320184 A1 | 12/2012 | Seyfried | |
| 2012/0325003 A1 | 12/2012 | Berger et al. | |
| 2013/0060085 A1 | 3/2013 | Anglopoulou et al. | |
| 2013/0310643 A1 | 11/2013 | Gora et al. | |
| 2015/0234155 A1* | 8/2015 | Lin | G02B 13/0085 359/622 |

OTHER PUBLICATIONS

Brian O. Flynn and Michael W. Davidson, "CCD Resolution for Optical Microscopy", MicroscopyU, Nikon.*
Ford, Tim N, Chu, Kengyeh K, Mertz, Jerome, Phase-gradient microscopy in thick tissue with oblique back-illumination, Oct. 28, 2012 online, Nature Methods, vol. 9 (Year: 2012).*
Written Opinion of the International Search Authority for PCT/US2015/010445 dated Apr. 13, 2015.
International Search Report from the International Search Authority for PCT/US2015/010445 dated Apr. 13, 2015.

* cited by examiner

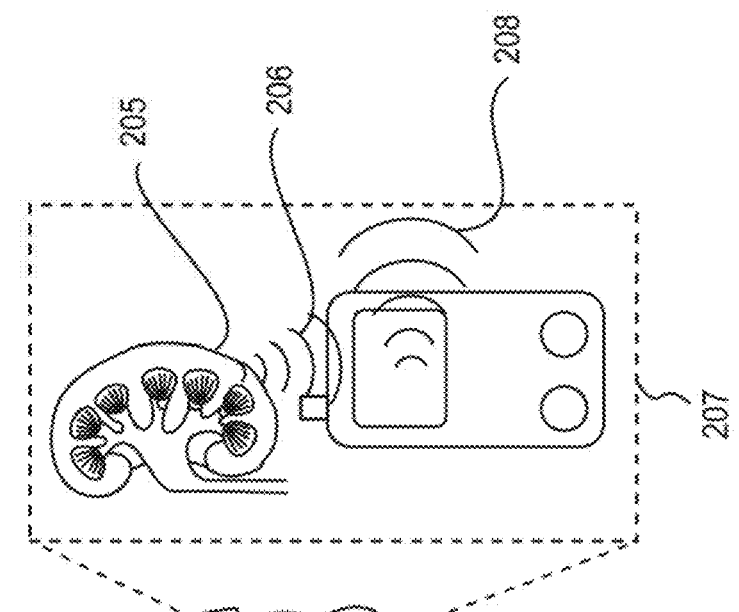
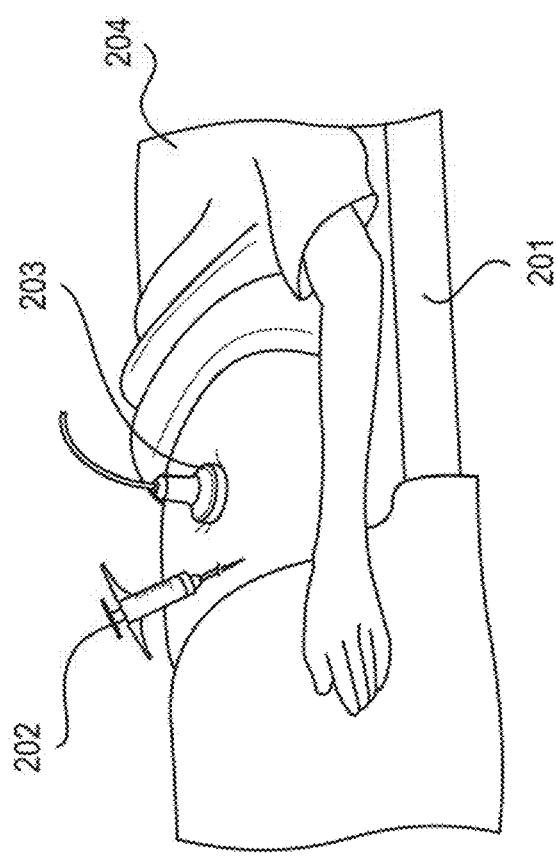
FIG. 2A
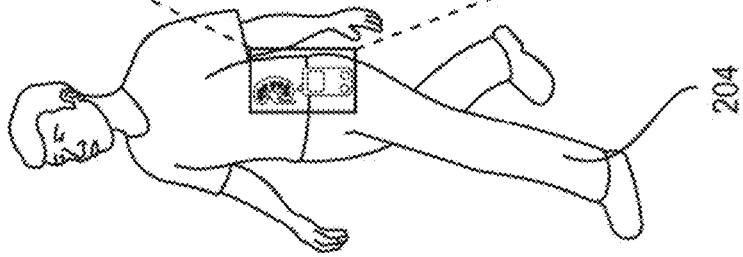
FIG. 2B

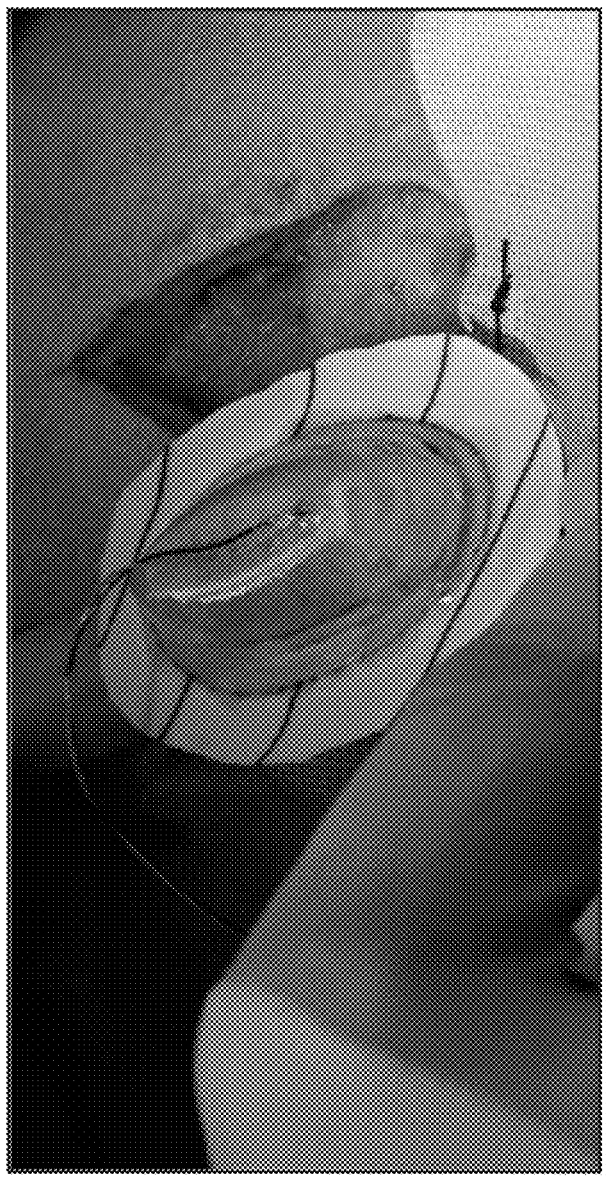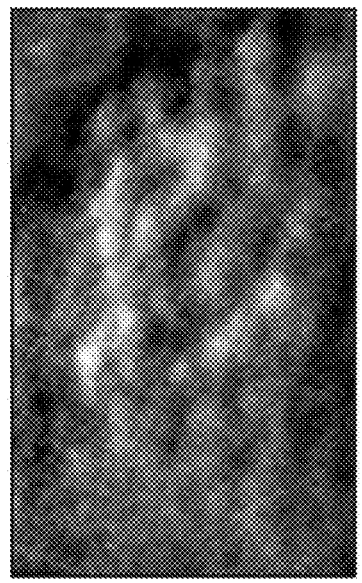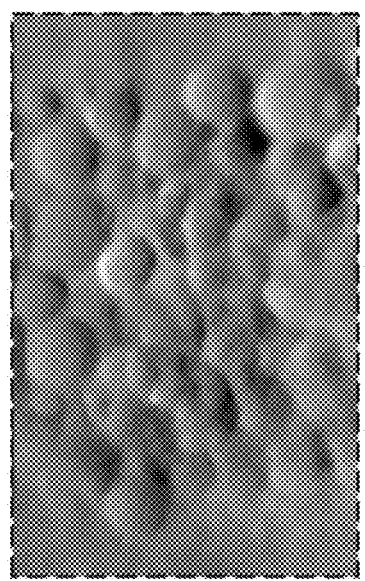
FIG. 11A
FIG. 11C
FIG. 11B

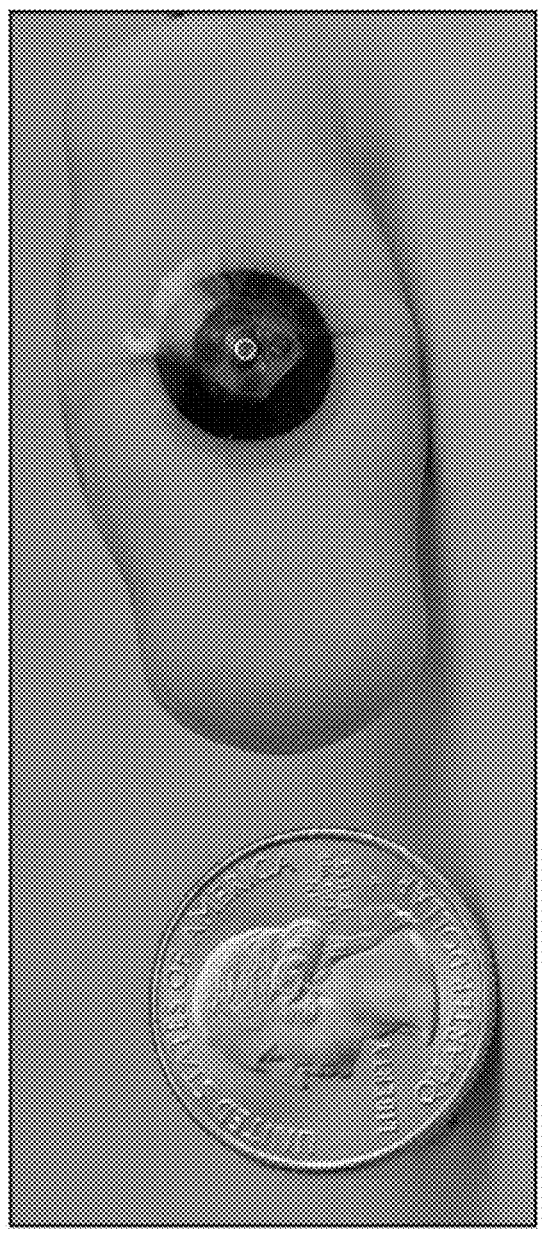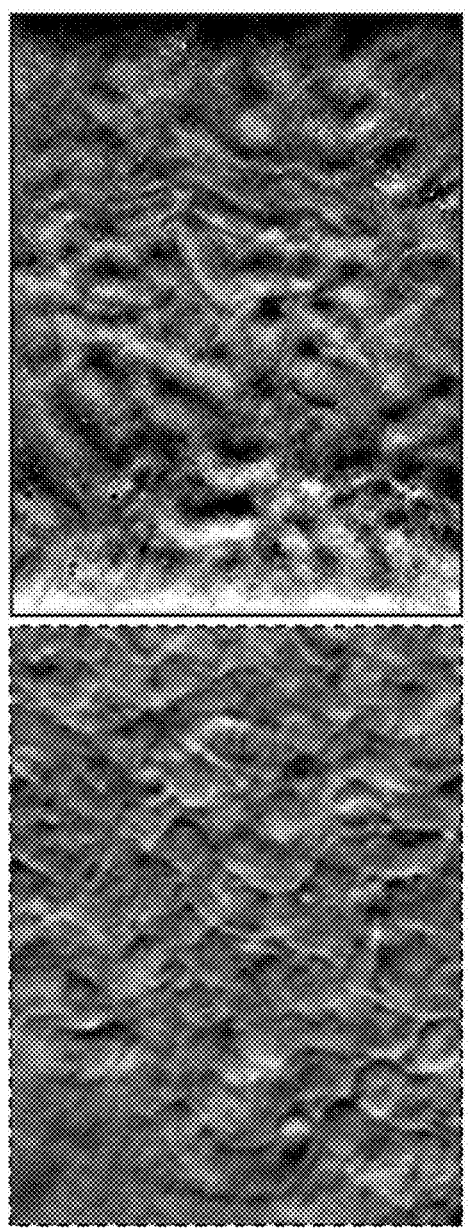
FIG. 12A
FIG. 12C
FIG. 12B

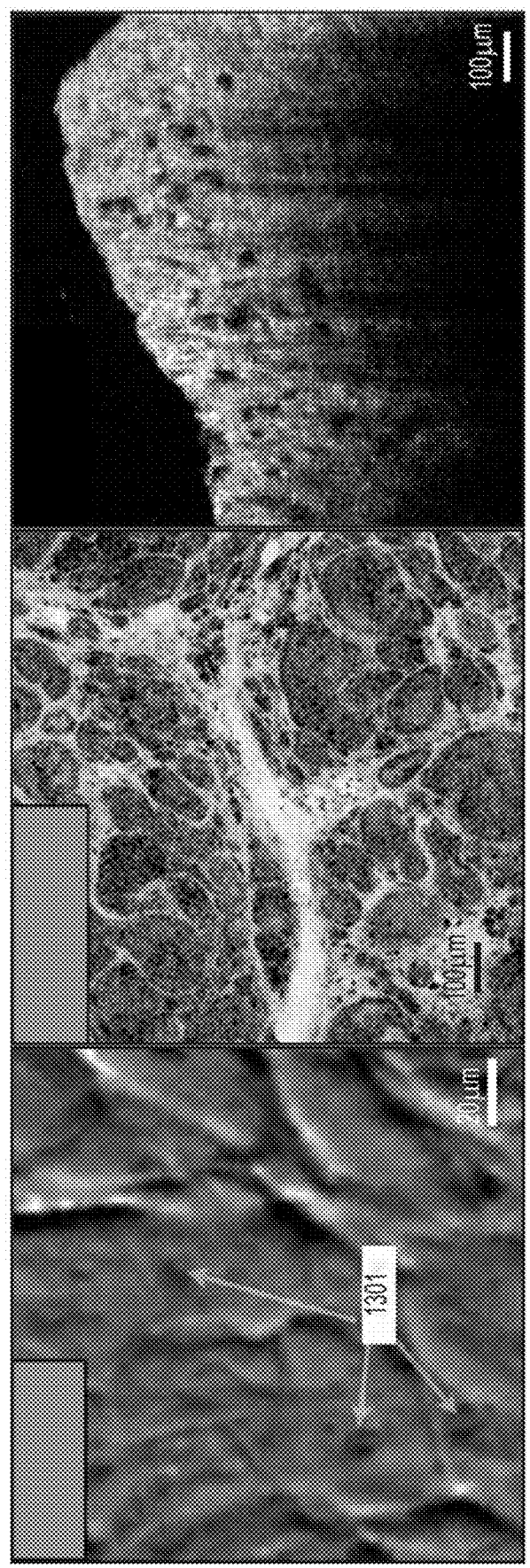

DETECTOR TO OUTPUT
ADDITIONAL DATA TO BE
TRANSMITTED WIRELESSLY
TO EXTERNAL DEVICE
OUTSIDE APPARATUS
USING TRANSMITTER
2201

FIG. 22

CONTROL ACTIVATION
OR DEACTIVATION OF
POWER SOURCE
2301

FIG. 23

METHOD AND APPARATUS FOR RECORDING MICROSCOPIC IMAGES FROM WITHIN A LIVING PERSON OR ORGANISM USING AN IMPLANTABLE DEVICE

CROSS REFERENCE TO RELATED APPLICATION(S)

The present application relates to and claims the benefit and priority from International Patent Application No. PCT/US2015/010445 filed Jan. 7, 2015, which claims the benefit and priority from U.S. Patent Application No. 61/924,574 filed on Jan. 7, 2014, the entire disclosures of which are incorporated herein by reference in their entireties.

FIELD OF THE DISCLOSURE

The present disclosure relates to microscopic imaging, and more particularly to exemplary embodiments of method and apparatus for recording microscopic images from within a living person or organism using an implantable device.

BACKGROUND INFORMATION

An application of optical imaging in biomedicine can be limited primarily by an inability of visible or near-infrared light to penetrate most tissue types. Imaging resolution from optical techniques can be typically largely superior to currently available diagnostic medical imaging techniques including magnetic resonance imaging (MRI), x-ray, x-ray computed tomography (CT), positron emission tomography (PET), single-photon emission computed tomography (SPECT), and ultrasound (US), which all lack the resolving power to distinguish individual cells within the body. The availability of cellular resolution imaging for diagnostic imaging would have extraordinary impact on medicine, as many pathologies are observable only through the examination of cellular structure.

However, high-resolution optical imaging may be available only for skin-deep external imaging or endoscopes that can probe luminal organs such as airways, blood vessels, and the reproductive and gastrointestinal tracts through tethered devices. The vast majority of organs within the body remain inaccessible to high-resolution optical imaging.

Accordingly, there may be a need to overcome at least some of the issues and/or deficiencies described herein above.

SUMMARY OF EXEMPLARY EMBODIMENTS OF PRESENT DISCLOSURE

To address and/or overcome the above-described problems and/or deficiencies, exemplary embodiments of method and apparatus for recording microscopic images from within a living person or organism using an implantable device can be provided.

To that end, according to an exemplary embodiment of the present disclosure, it is possible to utilize an implantable self-contained device that can contain an entire microscope apparatus that can be attached and/or inserted into a target organ through surgical access, and allowed to remain implanted to facilitate a long-term monitoring. For example, images or videos can be transmitted wirelessly to a receiving station for storage, display, or transmission via the Internet. A physician located many miles away would be able to directly view the cells in his or her patient, and make adjustments to treatment or diagnose the condition.

Further exemplary apparatus and method can be provided according to an exemplary embodiment of the present disclosure. For example, using at least one light source first arrangement, it is possible to provide pulses of light to at least one portion of a biological structure. At least one detector second arrangement can be used to detect images from the portion(s) based on the pulses, and provide data based on the detection. With at least one configuration, it is possible prevent and/or reduce a movement of the apparatus within at least one anatomical body (i) is a particular surface of the apparatus, (ii) covers at least one portion of the surface, and/or (iii) extends from the surface.

In addition or alternatively, with at least one computer third arrangement, it is possible to receive the data, and control a timing of at least one of activation or deactivation of at least one portion of the first arrangement based on the data.

For example, the control of the timing can be based on a frame-by-frame scheme associated with the images. A transmitter fourth arrangement can be connected to the second arrangement, whereas the second arrangement can be further configured to forward additional data to the fourth arrangement to be transmitted wirelessly to an external device that is outside the apparatus. The wireless transmission can include a radio frequency transmission. The fourth arrangement can include a further light source which is configured to wirelessly transmit the additional data by modulating light emission therefrom. Further, the fourth arrangement can be configured to wirelessly transmit the additional data by modulating the first arrangement.

According to another exemplary embodiment of the present disclosure, in operation, the apparatus can solely wirelessly communicate with an external device. Further, the third arrangement can be further configured to receive further data from the second arrangement which can include image data, and process the further data to generate information associated with microscopic data regarding the portion(s). At least one energy providing arrangement can be provided which can be configured to power the first, second and third arrangement. In addition, at least one magnetically-actuated switching arrangement can be provided which can be configured to actuate the energy providing arrangement within at least one biological sample when a magnetic arrangement is provided in or removed from a vicinity thereof. The energy providing arrangement can be recharged by the magnetic arrangement and/or a further induction arrangement. The third arrangement can be further configured to control the activation and/or the deactivation of the energy providing arrangement.

In yet another exemplary embodiment of the present disclosure, the first arrangement can include (i) at least two light-emitting diodes, (ii) at least one laser, and/or (iii) at least two super-luminescent diodes. For example, the illuminating laser diodes can provide the pulses that are passed through an oscillatory mechanism that is configured to reduce time-integrated laser speckle. The fourth arrangement can be further configured to receive additional data from the external device, and the third arrangement can be further configured to control at least one part of the first arrangement based on the additional data. The configuration(s) can be or include a photo-activatable coating. In addition, diffusive light guides can be provided into the outer housing of the apparatus to distribute the light output from a curing light source in order to evenly cure a photo-activatable coating on all surfaces of the device, including those not directly visible to the curing light source during implantation. The configuration(s) can include protrusions extending from the surface that are optical elements. Further, an optical arrangement can be provided which can be coupled to the detector arrangement, and which can include at least one liquid lens.

In still another exemplary embodiment, a power switch arrangement can be provided that is controlled by the third arrangement so as to actuate the power switch arrangement. For example, the third arrangement can include a further detector which detects a magnetic field strength from a source external from the biological structure, and the third arrangement can utilize information regarding the magnetic field strength to control the power switch arrangement. The combination of the first and second arrangement can perform an oblique back-illumination microscopy (OBM), a reflectance confocal microscopy (RCM), a widefield fluorescence microscopy, a fluorescence confocal microscopy (FCM), a spectrally encoded confocal microscopy (SECM), an optical coherence tomography (OCT), and/or a full-field optical coherence microscopy (FF-OCM).

Exemplary Video Processing and Wireless Activation/Communication

The exemplary implantable device according to an exemplary embodiment of the present disclosure can output exemplary microscopy images that can be transferred to an external station. The image data can take or have the form of analog video signals, such as, e.g., National Television System Committee (NTSC), sequential couleur à mémoire (SECAM), or Phase-Alternating Line (PAL), or can be in the form of digital signals. Since some exemplary camera modules can be self-contained and provide only analog outputs with no frame trigger input, it may be important to facilitate the camera's native frame timing to act as the master clock for other modules in the implantable apparatus. According to one exemplary embodiment of the present disclosure, for the exemplary OBM procedure(s), illumination source(s) from alternating directions can be switched on and off with a reliable frame synchronization.

In one exemplary embodiment of the present disclosure, the electronics module arrangement(s) (such as processor 615 of FIGS. 6A and 6B, or processor 715 of FIGS. 7A and 7B) of the exemplary implantable device can utilize the frame or interlaced sub-frame timing cues from the analog video output of the camera to trigger light source switching. One or more additional delays between the frame transition and the light source switching can also be introduced and/or utilized in the electronics to facilitate the time offset between the actual exposure time and the readout time of the camera.

According to the exemplary embodiment of the present disclosure, the exemplary implantable device can also include a mechanism using which it is possible to transfer the imaging data to the external station for viewing, storage, and/or retransmission. In one exemplary embodiment of the device, exemplary analog video signals from the camera module can be modulated on a radio frequency by the wireless transmitter, transmitted via an antenna, e.g., attached to or contained within the implantable device, received on a remote antenna attached to the external station, and/or demodulated by the electronics of the external station. Further, miniaturization can be achieved by providing an RF antenna into the inner surface of the device's housing using, for example, three-dimensional printing technology. An analog-to-digital converter (e.g., a "frame-grabber") can then be used to adapt the analog signal for digital processing and display.

In yet another exemplary embodiment of the present disclosure, the exemplary implantable device can include circuitry to process the camera output according to the exemplary OBM procedure(s) to generate phase-sensitive images as an intermediate substep before a wireless transmission. Because several raw frames are typically utilized to produce one or more processed frames, pre-processing the images within the exemplary implantable device before the transmission can reduce the transmission bandwidth requirement. Additionally, because compression artifacts in raw frames are amplified in the exemplary OBM procedure(s) (which amplifies low-contrast differences between raw images), a lossy image compression is not generally advantageous for raw image transmission, while can be acceptable and/or utilized for the exemplary processed images in a further reduction of bandwidth.

In still another exemplary embodiment of the present disclosure, the exemplary implantable device can also directly convert the camera output to a digital signal, which can then be encoded as a wireless transmission, or processed on-board the implantable device as described herein above.

In a further exemplary embodiment of the present disclosure, the wireless transmission between the exemplary implantable device and the external station can utilize a non-radio frequency transmission. For example, red light and/or infrared light can be modulated with an encoded signal for one-way and/or two-way communication, since such wavelengths can be weakly absorbed by typical tissue, and provide a window for optical communication.

For example, the modulated light source used for one- and/or two-way communication can be provided by, e.g., distinct and separate illumination source(s) from the primary light source used to illuminate the biological structure. In this exemplary case, the light sources can be distinguished by wavelength multiplexing (e.g., the area sensor can be made sensitive to the primary light source and not the communication light source using a color filter) or by time multiplexing (i.e. the primary light source is activated and the communication light source is deactivated during a first duration while image data can be acquired; subsequently the primary light source can be deactivated and the communication light source can be activated during a second duration while the image data is transmitted to a separate light receptor and demodulator positioned outside of the biological structure). This two-phase procedure can then continue in a cyclical manner for continuous imaging.

Further miniaturization and electrical power efficiency can be achieved by modulating the primary light source for communication during the image data acquisition time period. In this single-phase procedure, image data from a single frame is stored in a temporary data storage device (e.g. flash memory or a secondary pixel layer in a frame-transfer area sensor). For example, when a subsequent frame is acquired, the first data from the data storage device can be communicated outside the body simultaneously by modulating the intensity of the primary light source. The modulation frequency for communication should be higher (e.g., greater than one order of magnitude higher in temporal frequency) than the inverse of the exposure time to ensure no temporal flickering artifact is observed in the current image acquisition. Furthermore, the modulation scheme can be, utilize and/or include a constant envelope to provide temporally stable illumination for the current image acquisition and promote efficient electrical power consumption. Exemplary modulation schemes, such as phase-shift keying (PSK) or frequency-shift keying (FSK) feature, can effectuate such exemplary constant envelope modulation. Differential phase-shift keying (DPSK) schemes can be compatible with the exemplary method and system according to various exemplary embodiments as no secondary reference modulation is required for the receiver and demodulation apparatus.

In yet another exemplary embodiment of the present disclosure, a transmitter module can be provided that designed to modulate the analog video into an analog television channel. In this exemplary case, because television channel transmitters and receivers can be configured for a synchronized broadcast of both video and audio, and the implantable microscopy system according to an exemplary embodiment of the present disclosure can produce, e.g., soundless images, the audio channel corresponding to the analog television video channel selected for microscopy image transmission is available for the transmission of additional data, which can include exposure parameters, power supply status, and/or (with the inclusion of additional sensor module(s)) device localization.

Exemplary Power Supply for Exemplary Implantable Device

According an exemplary embodiment of the present disclosure, the power supply for the implantable device is entirely encased within the housing of the apparatus. Additional miniaturization of the exemplary apparatus can be achieved by providing a battery into the housing material in a three-dimensional shape such that volume not occupied by other optical, electrical, or mechanical components of the apparatus can be filled with battery components. Such exemplary three-dimensional batteries can be provided into the inner surface of the housing using three-dimensional printing technologies. Several high-density electrochemical storage densities can be available, and may be appropriate for the exemplary implantable device, included lithium ion, lithium polymer, and silver oxide. High capacitance devices, such as supercapacitors, can also serve as power sources.

Because the power source(s) can be physically confined and isolated by the implantable device housing, traditional charging via physical contact of electrical wires is not appropriate for the intended application of the invention. Therefore, in another exemplary embodiment of the present disclosure, the exemplary implantable device can include one or more mechanisms for replenishing the electrical power supply through one or more implementations of wireless charging. One exemplary implementation can be an inductive charging, whereby an externally-driven oscillating magnetic field induces current flow through an inductive coil within the implantable device, which can then be used to charge the battery or another power source.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying drawings showing illustrative embodiments of the present disclosure, in which:

FIGS. 2A and 2B are diagrams of the apparatus and implantation method according to another exemplary embodiment of the present disclosure.

FIG. 11A is a photograph of the system according to yet another exemplary embodiment of the present disclosure;

FIGS. 11B and 11C are illustrations of exemplary microscope image data obtained using the system of FIG. 11A and from a non-miniaturized conventional benchtop microscope system, respectively;

FIG. 12A is a photograph of the system according to yet further prototype exemplary embodiment of the present disclosure;

FIGS. 12B and 12C are illustration of exemplary microscope image data obtained from the system of FIG. 12A, and from the non-miniaturized conventional benchtop microscope system;

FIGS. 13A-13C are exemplary microscope images of tissue obtained using exemplary optical microscope modalities which may be utilized by the systems according to various exemplary embodiments of the present disclosure;

FIGS. 18-23 present additional features of an apparatus according to embodiments of the invention.

Figure 1:
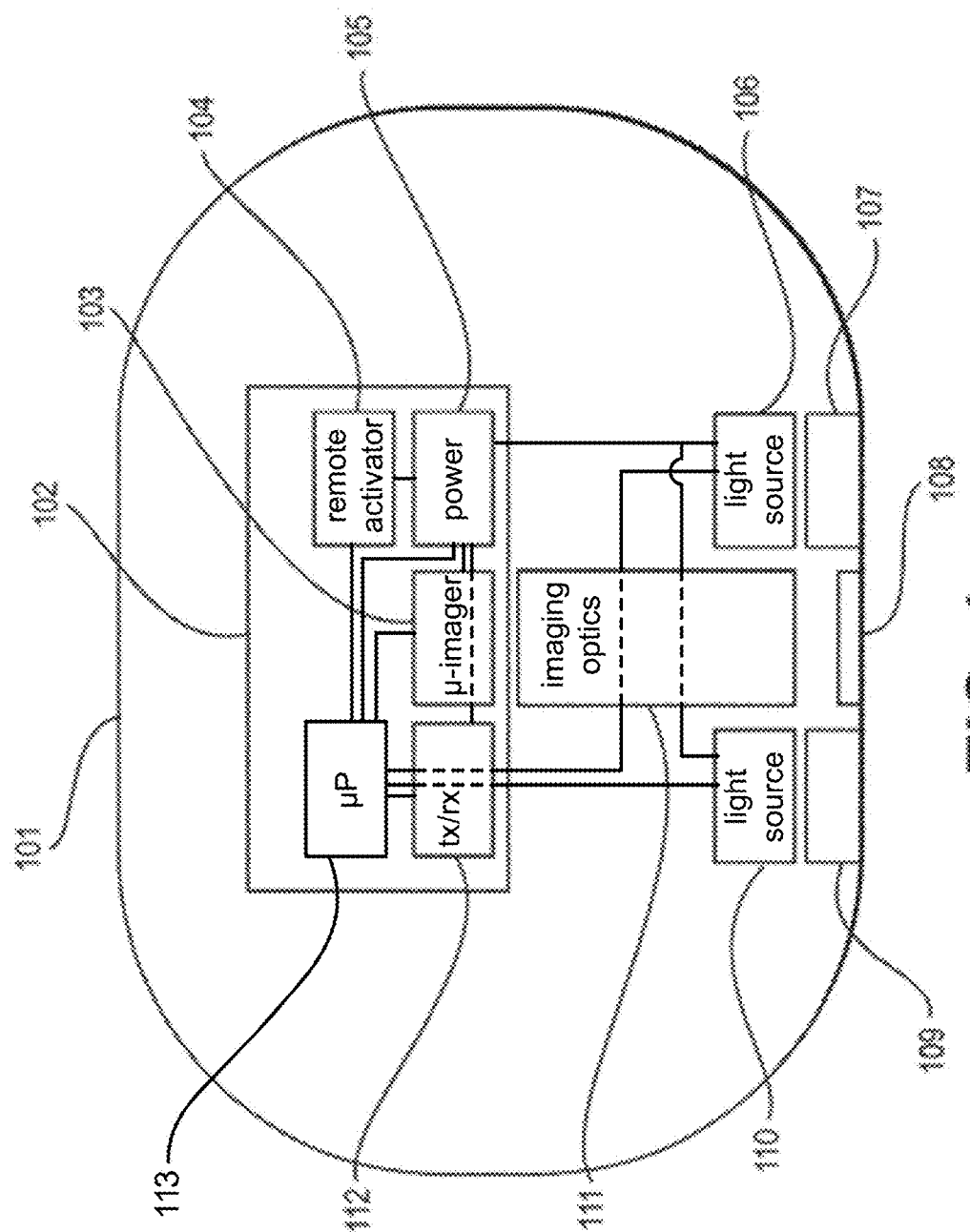
FIG. 1 is a block diagram of an apparatus according to an exemplary embodiment of the present disclosure.

Throughout the figures, the same reference numerals and characters, unless otherwise stated, are used to denote like features, elements, components or portions of the illustrated embodiments. Moreover, while the subject description will now be described in detail with reference to the figures, it is done so in connection with the illustrative embodiments. It is intended that changes and modifications can be made to the described embodiments without departing from the true scope and spirit of the subject disclosure and appended claims.

DETAILED DESCRIPTION OF EXEMPLARY EMBODIMENTS

Exemplary Implantable Capsules

Various exemplary embodiments of the present disclosure is based on a concept of, e.g., a self-contained device which can be implanted within or upon an organ that captures high-resolution optical images, and transmits the images to a recording and display system located external to the body. An exemplary arrangement of components is shown in an exemplary embodiment of such exemplary system as illustrated in FIG. 1. For example, an outer housing 101 can isolate and contain most or all components of the exemplary system in a biological imaging environment. An electric circuit board 102 including microprocessor 113 can includes and/or host modules that can facilitated a remote power activation 104, provide an electrical power 105, provide a radio-frequency wireless communication 112 that can transmit imaging data to an external storage module, and/or detect light or other electromagnetic radiation to form a microscopic image 103. The microscopic imaging arrangement in this exemplary system of FIG. 1 can comprise an optical imaging arrangement 111 and an optical window 108 so as to interface the exemplary optics with the exterior of the housing. Light sources 106, 110 (or other electromagnetic radiation sources) can generate illumination, which can be conducted to the imaging sample via or through light/radiation guide modules 107, 109.

Figure 18:
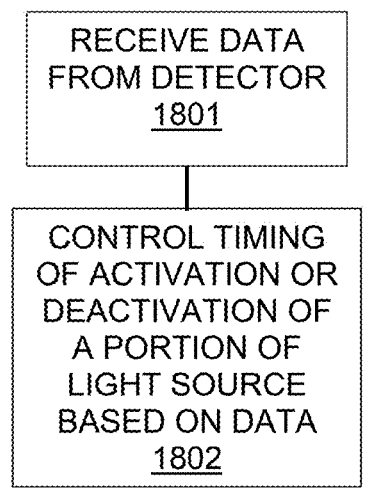
Figure 19:
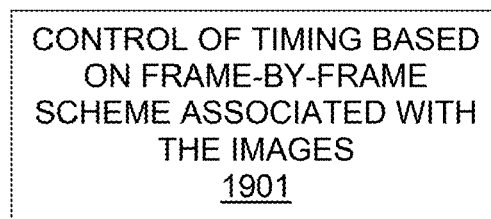
Figure 20:
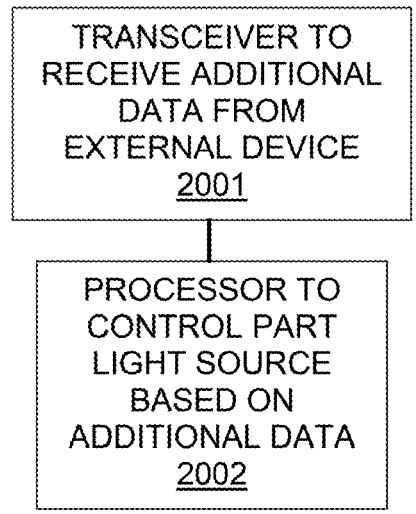
Figure 21:
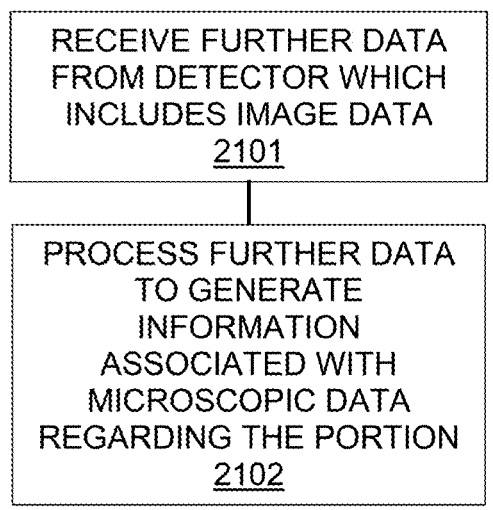

In various embodiments the apparatus may include a processor which is configured to receive the data 1801, and control a timing of at least one of activation or deactivation of at least one portion of the at least one light source based on the data 1802 (FIG. 18). In other embodiments of the apparatus, the control of the timing may be based on a frame-by-frame scheme associated with the images 1901 (FIG. 19). In still other embodiments, the apparatus may include a transceiver configured to receive additional data from the external device 2001, wherein the processor is further configured to control at least one part of the at least one light source based on the additional data 2002 (FIG. 20). In yet other embodiments of the apparatus, the processor may be further configured to receive further data from the at least one detector which includes image data 2101, and process the further data to generate information associated with microscopic data regarding the at least one portion 2102 (FIG. 21). In still other embodiments, the apparatus may include a transmitter which is coupled to the at least one detector, wherein the at least one detector is further configured to output additional data to be transmitted wirelessly to an external device that is outside the apparatus using the transmitter 2201 (FIG. 22). In yet other embodiments, the apparatus may include a processor which is configured to control the activation or the deactivation of the power source 2301 (FIG. 23).

Exemplary Implantation and Organ Monitoring Method

According to an exemplary embodiment of the present disclosure, a self-contained device may be used which can have a package sized that is similar to approximately a grain of rice (~1 mm in diameter and 5 mm in length). As illustrated in FIG. 2A, the device can be positioned (implanted) into an organ of interest (e.g. the kidney) inside a sedated patient (201). The exemplary device can be delivered with a syringe and needle (202), e.g., with or without secondary imaging guidance (e.g. an ultra-sound guide 203). Once positioned, the patient (204) can recover and act freely without being restricted to a hospital location or tethered to recording equipment, as illustrated in FIG. 2B. The exemplary device (205) can then periodically or continuously illuminate and/or detect image data from the organ of interest. This image data can be wirelessly communicated (206) to a wearable electronic recording device (e.g. smart phone, smart watch, etc. 207). This wearable recording device (207) can store the image data and/or further transmit copies of the image data (208) to a physician or another professional (e.g., respective computers thereof) in a remote location far from the patient.

Exemplary Implantable Capsule with Tethered Sub-Modules

Figure 3A:
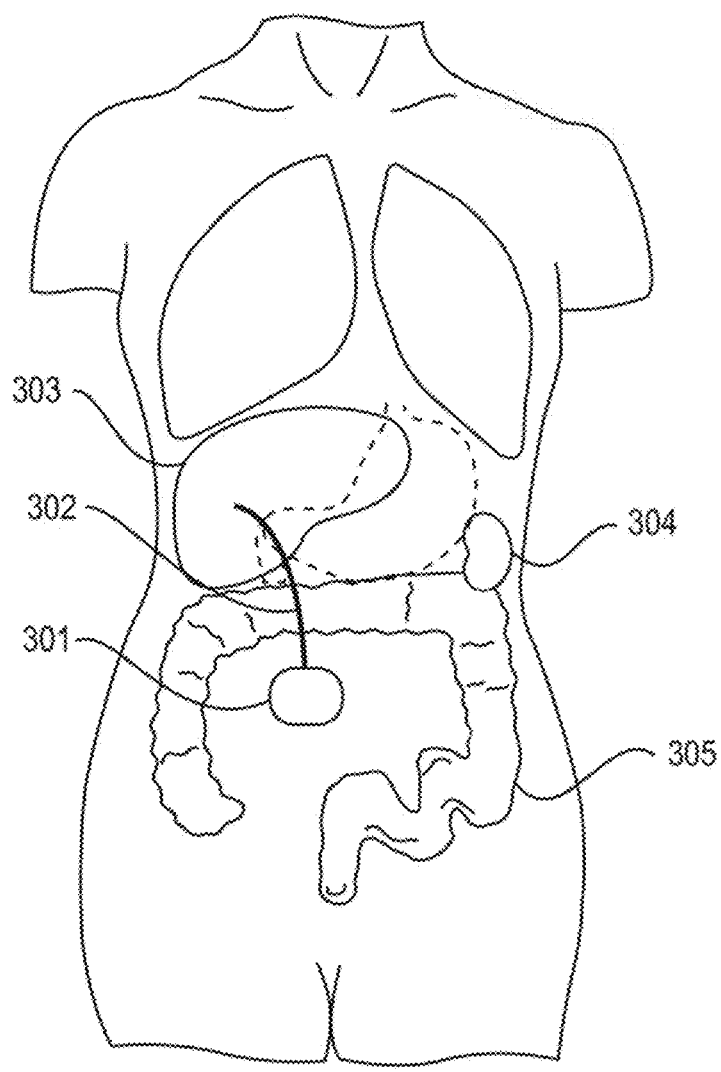
FIGS. 3A and 3B are views of the system according to a further exemplary embodiment of the present disclosure implanted in the human body.
Figure 3B:
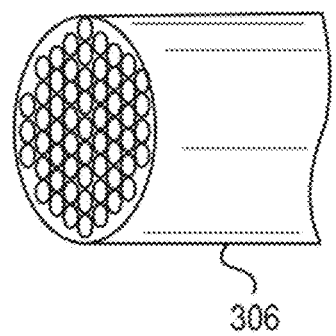

According to another exemplary embodiment of the present disclosure, the self-contained system does not have to be a single solid apparatus, and can be divided into sub-modules that can interface with a central implanted module, as illustrated in FIG. 3. As shown in FIG. 3A, a central module 301 of the exemplary system can include the bulk of the optics, electronics, and/or communications circuitry can be implanted at any convenient location. Optical probes can then branch from the central device 301 via, e.g., flexible electrical or optical (e.g., flexible) connectors 302 and be implanted in organ systems that utilize microscopic monitoring, such as, e.g., the liver 303, kidney 304, and/or the gastrointestinal tract 305. According to an exemplary embodiment, flexible optical connectors 302 can be comprised, for example, of small (~300 micron diameter) imaging fiber bundles 306 that can be bonded to organs of interest, as illustrated in FIG. 3B. Exemplary images from the distal faces of the fiber bundle can be transmitted to the larger central implanted module containing other optical and electrical components. The flexible optical connectors 302 can transmit both illumination and return radiation (e.g., bi-directional), and/or separate flexible optical connectors can be used for illumination and return radiation, respectively.

Exemplary Implantable Capsule Interfaces with Organs

Figure 4B:
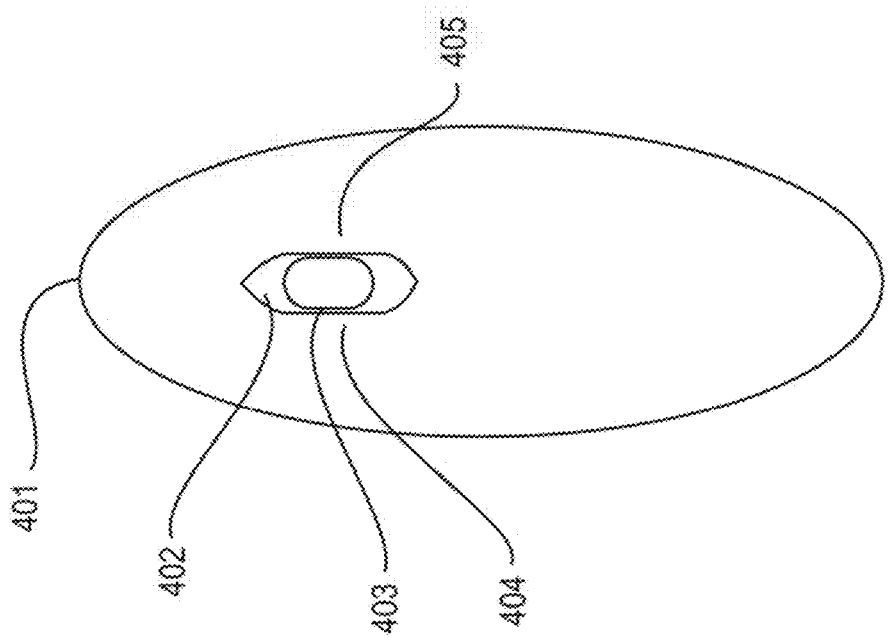
FIGS. 4A and 4B are cross-sectional and exterior views of an exemplary arrangement of an implantable capsule of the system according to an exemplary embodiment of the present disclosure within an organ for the purpose of microscopic imaging.
Figure 4A:
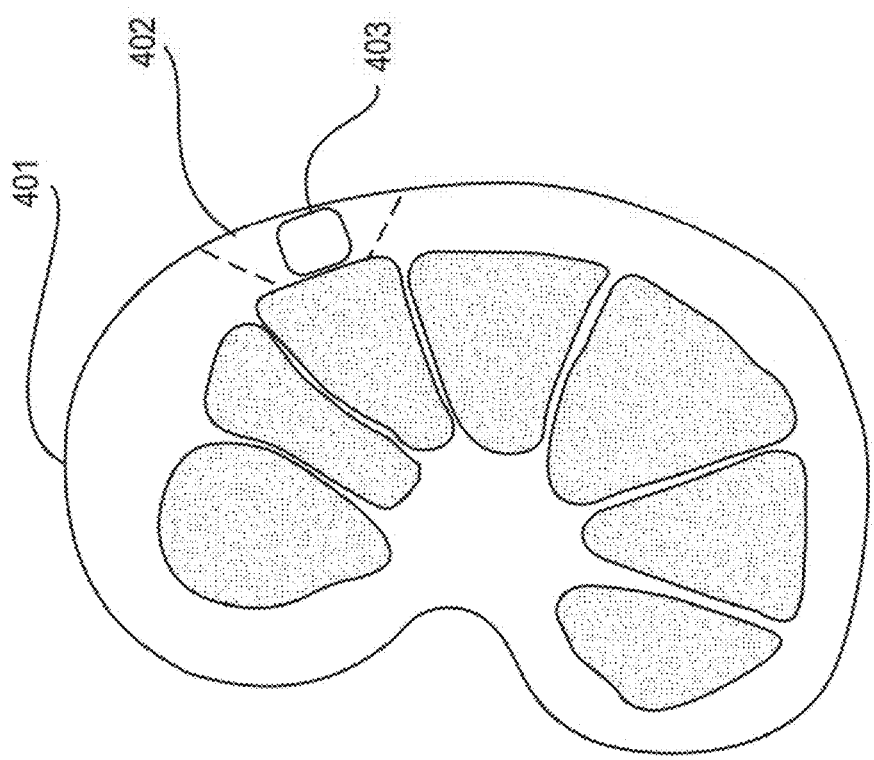
Figure 5B:
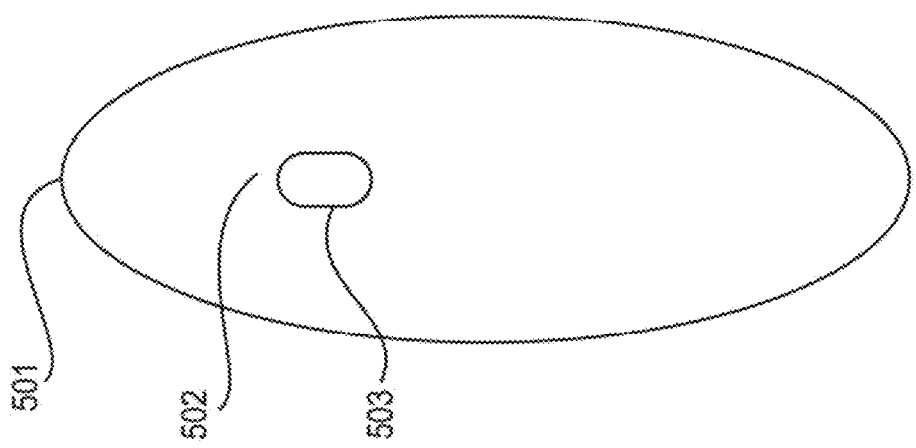
FIGS. 5A and 5B are cross-sectional and exterior views of an exemplary arrangement of the implantable capsule of the system according to another exemplary embodiment of the present disclosure contiguous with an organ for the purpose of superficial microscopic imaging.
Figure 5A:
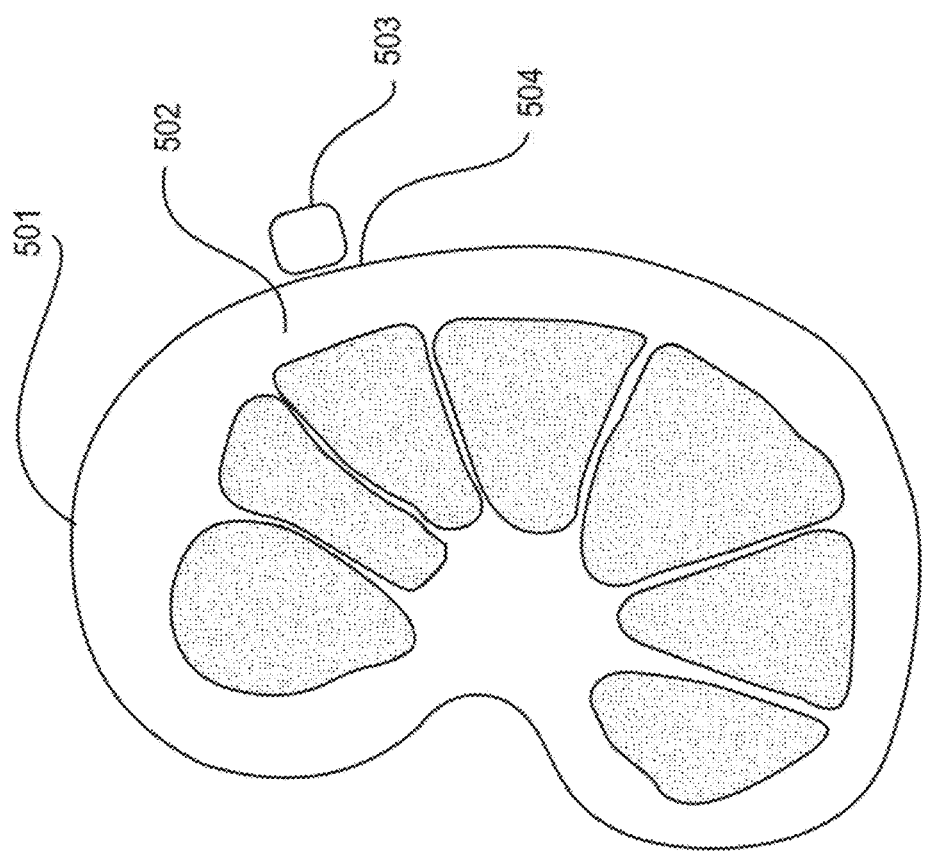

FIGS. 4A and 4B illustrate cross-sectional and exterior views of an exemplary arrangement of an implantable capsule of the system according to an exemplary embodiment of the present disclosure within an organ for the purpose of microscopic imaging. The exemplary organ 401 is illustrated in FIGS. 4A and 4B is a kidney. An incision 402 can be made into the organ 401 to admit an implanted device 403 of the exemplary arrangement. Depending on an exemplary configuration of the implanted device 403, the imaging region of interest of the sample 401 can be located in any direction adjacent to the device 403, for example at location(s) 404 or 405. The exemplary device 403 can also be simultaneously or sequentially image the regions of interest 404, 405. FIGS. 5A and 5B illustrate cross-sectional and exterior views of a further exemplary arrangement of an implantable capsule of the system according to an exemplary embodiment of the present disclosure that is provided within an organ for the purpose of superficial microscopic imaging. The exemplary organ 501, which is illustrated in FIGS. 5A and 5B, is a kidney. A surface location 502 can be identified on the organ 501 to support an implanted device 503 of the exemplary arrangement. This exemplary configuration of the implanted device 503 can identify the imaging region of interest of the sample 501 that can be located at the device-organ interface 504. The exemplary device 503 can also be simultaneously or sequentially image the regions of interest 504, 505.

Exemplary Implantable Capsules

Figure 6A:
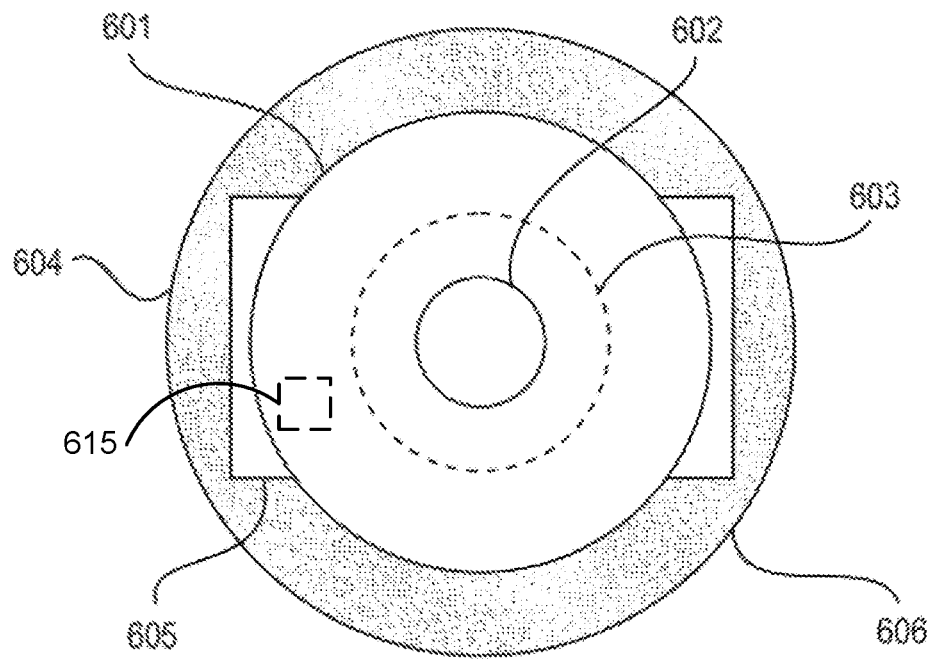
FIGS. 6A and 6B are top and side cross-sectional views, respectively, of an exemplary configuration of the implantable device according to an exemplary embodiment of the present disclosure that can generate microscopic images.
Figure 6B:
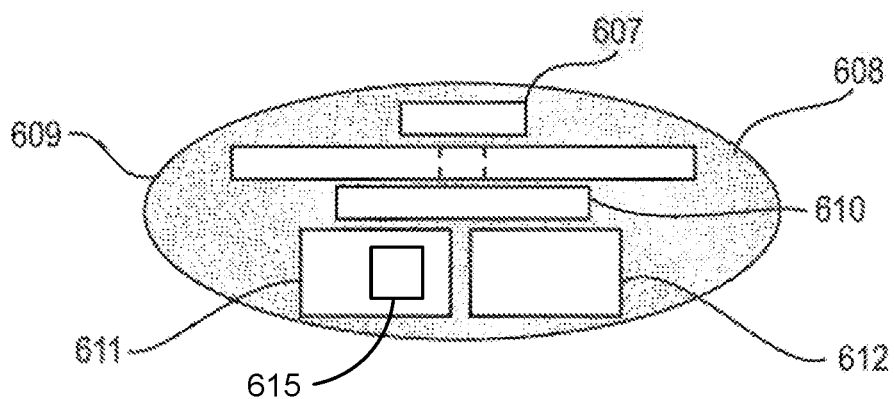

FIGS. 6A and 6B show top and side cross-sectional views an exemplary configuration of an implantable device according to an exemplary embodiment of the present disclosure that generates phase-sensitive images of cells within a thick scattering medium.

This exemplary embodiment can include (i) one or more electronics modules 601, 608 that can have multiple components for interfacing and controlling the other modules of the exemplary device, (ii) one or more lens modules 602, 607 which can be used to image a region of the sample outside the capsule/device to one or more camera module(s) 603, 610, and (iii) one or more transmitters 605, 611 which can be configured to transmit exemplary images to and/or receive instructions/data/signals from an external station. A computer arrangement or processor 615 is also provided and configured to control a timing of at least one of activation or deactivation of at least one portion of the at least one light source to synchronize between an exposure time and a readout time. The exemplary electronic components of the device shown in FIGS. 6A and 6B can be powered by one or more batteries 606, 612 and/or or other power source(s). According to one exemplary variant, the entire device can be encased in a capsule housing arrangement 604, 609 that can be compatible with a live organ implantation.

Figure 7A:
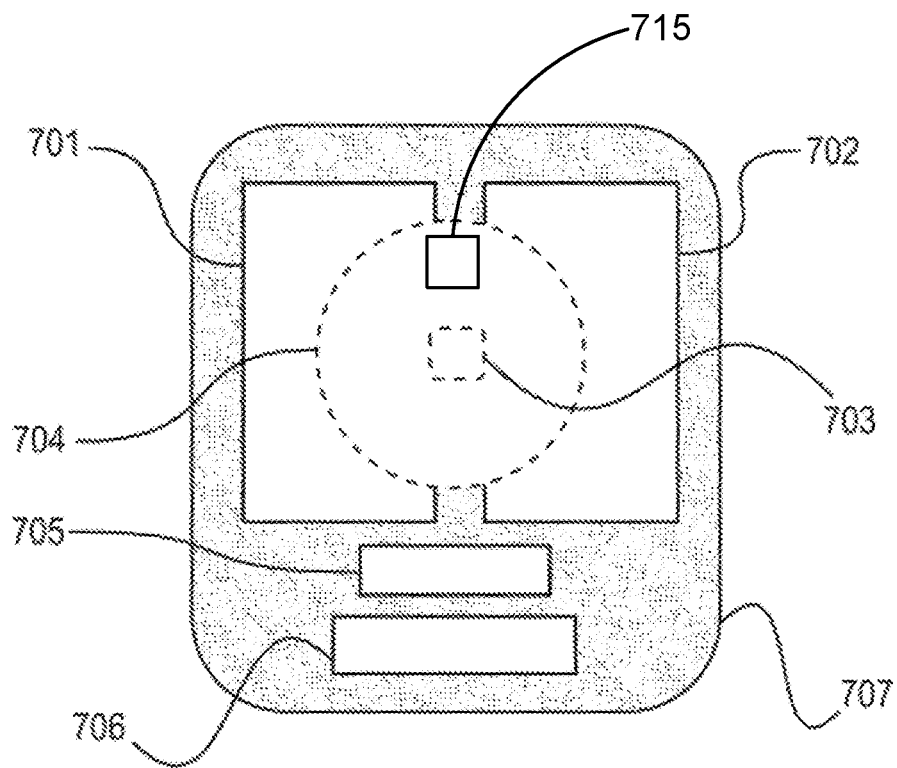
FIGS. 7A and 7B are top and side cross-sectional views a further exemplary configuration of the implantable device according to another exemplary embodiment of the present disclosure that can generate microscopic images.
Figure 7B:
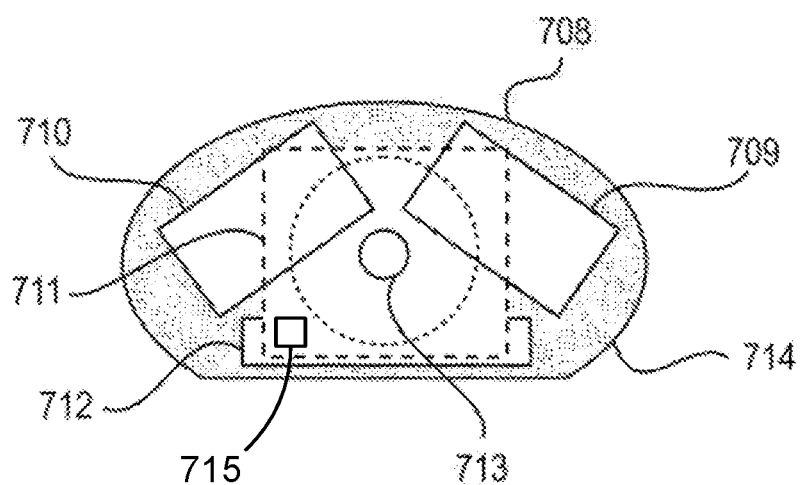

FIGS. 7A and 7B show top and side cross-sectional views an exemplary configuration of the implantable device (e.g., the capsule) according to another exemplary embodiment of the present disclosure which is similar to the exemplary device shown in FIG. 6.

As shown in FIG. 7, the exemplary device can include one or more electronics main board arrangements 704, 711, one or more camera sensor arrangements 705, 708, one or more transmitter arrangements 702, 710), one or more (e.g., battery) power source arrangements 701, 709, and one or more capsule housings 707, 714. A computer arrangement or processor 715 is also provided and configured to control a timing of at least one of activation or deactivation of at least one portion of the at least one light source to synchronize between an exposure time and a readout time. This exemplary device according to the further exemplary embodiment of the present disclosure can utilize and/or include one or more optical arrangements 703, 713 that can comprise a reflective mirror element/arrangement so as to fold the optical axis by, e.g., approximately 90 degrees to achieve an imaging plane that can be perpendicular to the plane of the image sensor arrangements 705, 708. The main board arrangement(s) 704, 712 can also be configured to place the illumination source(s) in a close proximity to the imaging plane and with a physical aperture to admit the imaging beam path.

Figure 8B:
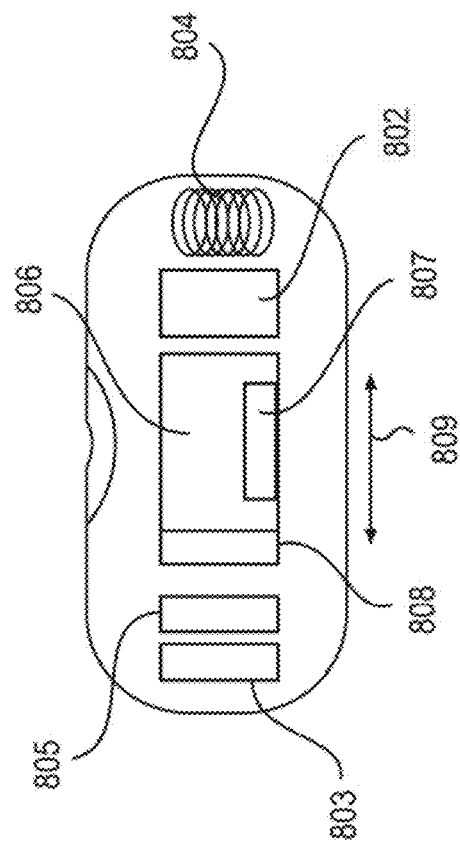
FIGS. 8A and 8B are diagrams of front and side view of of yet a further exemplary configuration of the implantable device according to a further exemplary embodiment of the present disclosure.
Figure 8A:
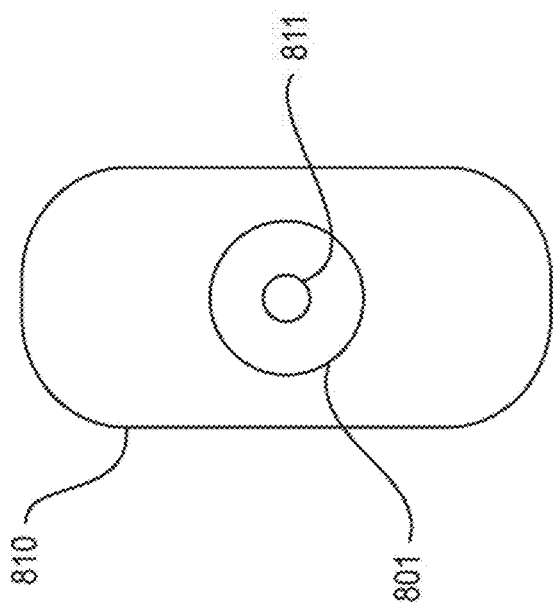

FIGS. 8A and 8B show front and side view of exemplary internal components of a wireless microscope implant system/apparatus (801) according to a yet further exemplary embodiment of the present disclosure. The exemplary system/apparatus 801 can include, e.g., a microbattery (802), a wireless transmitter (803), an antenna (804), electronics (805), an optics module (806) that can contain a light source (807), a camera (808), and the micro-optics that can distinguish each imaging modality (e.g. OBM, SECM, OCT, etc.). Optionally, an element (such as, e.g., a micromotor) can move one or more of the internal components of the exemplary system/apparatus (801) to scan a larger field of view (809) or change the image plane within the surrounding tissue. Many or all of these exemplary components should fit inside a biocompatible outer housing (810) that contains optical windows (811) that can facilitate or allow light or other electromagnetic radiation to pass through the exemplary WIM device (801). The entire exemplary device (801) can be self-contained; and/or, e.g., the active components, including the control circuit, transceiver, camera, and light source(s) can be battery powered using the microbattery (802).

Exemplary Implantable Capsule Microscope Modalities

Figure 9A:
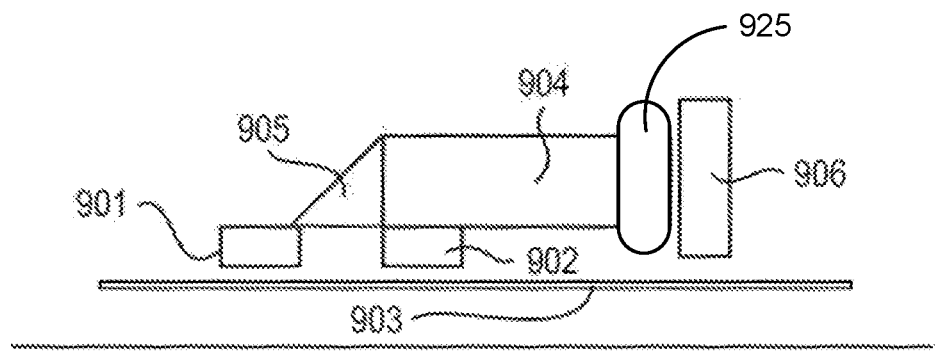
FIG. 9A-9C are side views of of exemplary compact and miniature optical arrangements which may be utilized in and according to various exemplary embodiments of the present disclosure.
Figure 9B:
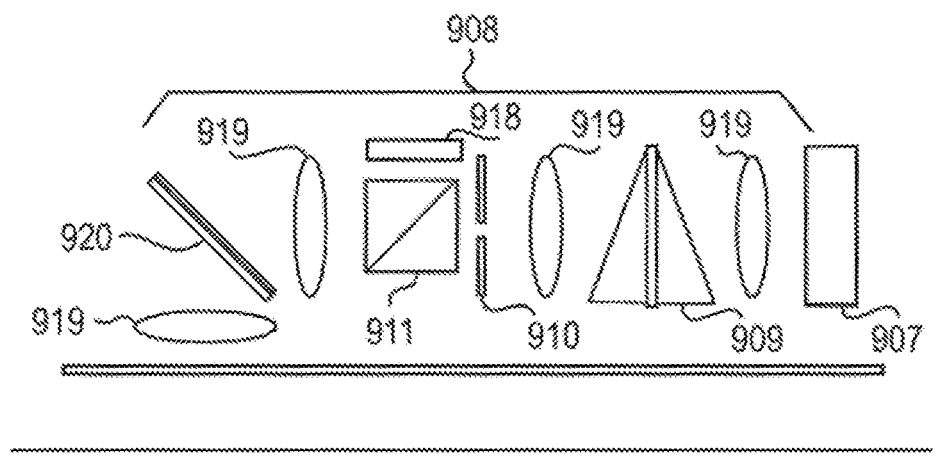
Figure 9C:
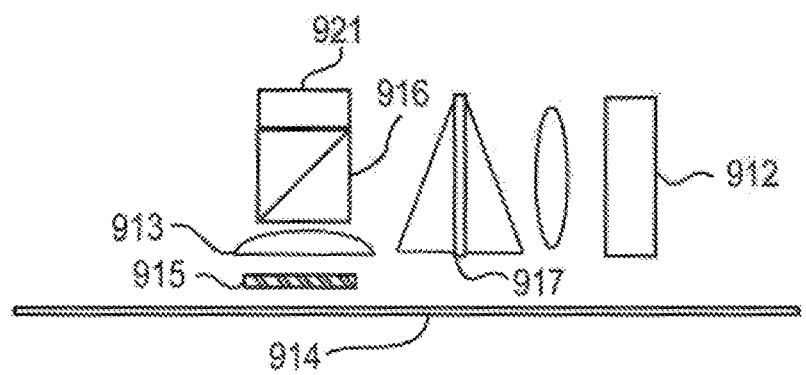

FIG. 9 shows side views of exemplary compact and miniature optical arrangements which can be utilized for exemplary microscopy modalities that can be implemented in the exemplary embodiments of the present disclosure. For example, FIG. 9A shows the exemplary arrangement that includes an oblique back-illumination microscopy (OBM), FIG. 9B shows an exemplary arrangement for providing spectrally-encoded confocal microscopy (SECM), and FIG. 9C illustrates an exemplary arrangement facilitating an optical coherence tomography (OCT) modality.

The exemplary arrangement providing the OBM that is one of the exemplary technologies is illustrated in FIG. 9A, and can be used with the exemplary devices according to the exemplary embodiments of the present disclosure. For example, using such arrangement/system, light or other electromagnetic radiation can diffuse from at least two incoherent light sources 901 and 902 through tissue 903, and can back-illuminate the superficial microstructures at an oblique angle. By subtracting two images that are obtained using illumination from different sources, a phase microscopy image is formed. A gradient index (GRIN) objective lens 904 and a side-viewing prism 905 can be used therewith.

For example, using such exemplary configuration, a compact optical system can be provided, which may be further miniaturized, for example, with custom aspheric micro-optics 925 made in-house, using, e.g. a diamond turning lathe and injection molding equipment. A multiple-pixel area sensor 906 can be used to detect return radiation originating from each of the light sources 901, 902.

As illustrated in FIG. 9B, the exemplary microscopy modality SECM can be implemented efficiently in an exemplary scanning-less configuration. The exemplary elimination of scanning can be accomplished, e.g., by acquiring multiple line spectra at the same time on an area detector 907 instead of the conventional line detector. Additional space savings can be achieved by, e.g., a monolithic construction of a number or many of the micro-optical components (including, e.g., lenses 919 and a grating 920) on a single substrate 908. For example, the optical component that separates the broadband SECM light (e.g., a light-emitting diode 918) into its constituent wavelengths can be or include, e.g., a prism-grating-prism (PGP, 909). The confocal slit 910, that can replace the conventional pinhole, can be deposited as a metal coating directly onto the beam-splitter 911, produced, e.g. with computer numerical controlled (CNC) mill and micro-bonder equipment.

Similarly to the previously described exemplary configuration for SECM of FIG. 9B, FIG. 9C illustrates an exemplary configuration for utilizing the OCT modality for the exemplary WIM device. It is possible to utilize a parallelize acquisition to obtain multiple A-lines at the same time by using a camera 912 instead of, e.g., a line detector, thus reducing and/or eliminating beam scanning. A cylindrical micro-lens 913 can project a vertical sheet of light from broadband light source (e.g., a superluminescent diode 921) into the tissue 914. According to an exemplary embodiment, it is possible to integrate both the sample and reference arms into the same physical path by, e.g., placing a partial reflector 915 in the beam path, which is known as a common-path configuration. The combined light 916 can be redirected to a PGP 917 with its diffraction axis perpendicular to the line's illumination axis. The video camera 912 can then detect a two-dimensional image where one dimension represents spatial location on the sample and the other dimension is wavelength. A cross-sectional image can then be reconstructed by performing the Fourier transform of each spectral interference pattern that can results from the coherent combination of reference arm light (or other radiation) and sample arm light (or other radiation) from each illuminated location on the sample.

Exemplary Implantable Capsules Using Oblique Back-Illumination Microscopy

Figure 10A:
FIG. 10A is a photograph of the system according to still another exemplary embodiment of the present disclosure.
Figure 10B:
FIG. 10B is an illustration of an exemplary microscope image data obtained using the system of FIG. 10A.

FIG. 10A shows an image of an exemplary implantable capsule according to the exemplary embodiment of the present disclosure. This exemplary capsule can measure approximately 1 inch in length and 0.5 inch in height and width, and can utilize oblique back-illumination microscopy (OBM) with, e.g., four illumination sources arranged around one detector optical arrangement and area sensor. Image data can be wirelessly transmitted using, e.g., a 433 MHz RF transmitter. The exemplary device can be remotely activated by the presence of a magnetic field. FIG. 10B shows a processed OBM image of a glass bead in an exemplary scattering tissue phantom showing phase gradient contrast. Field of view can be approximately 250 microns.

FIG. 11A shows an image of a further exemplary implantable capsule according to yet another exemplary embodiment of the present disclosure. This exemplary capsule can include a smooth, domed housing that can enhance biocompatibility and device stability when implanted in a subdermal location. The housing can measure approximately 45 mm in length and 20 mm in diameter. This exemplary device can implement an oblique back-illumination (OBM) with four illumination sources and transmits image data wirelessly using a 2.4 GHz RF transmitter. The exemplary device can include a micro-controller that can activate and deactivate the imaging according to a pre-programmed strobe pattern. The device strobing can be further activated and deactivated by a magnetic switch that engages in the presence of a magnetic field. The device of FIG. 11A is illustrated in a configuration during a sub-dermal implantation starting a 2-week survival study in adult swine. FIG. 11B shows an exemplary OBM image of porcine adipocytes acquired ex-vivo with a non-miniaturized benchtop setup. The exemplary field of view is approximately 300 microns. FIG. 11C shows an exemplary OBM image of porcine adipocytes acquired in-vivo with the device shown in FIG. 11A during a 1-week live animal implant study. The image in FIG. 11C was transmitted wirelessly from the battery powered device approximately 4 days after surgical implantation.

FIG. 12A shows an image of another exemplary implantable capsule according to still another exemplary embodiment of the present disclosure. This exemplary capsule can measure approximately 45 mm in length and 20 mm in diameter, and is shown next to a standard United States quarter dollar for the exemplary size reference. This exemplary device can implement the oblique back-illumination (OBM) modality with a number of (e.g., four) illumination sources, and can transmit image data wirelessly using a 2.4 GHz RF transmitter. The exemplary device of FIG. 12A can include a micro-controller that activates and deactivates the imaging according to a pre-programmed strobe pattern. The exemplary device can provide strobing that can be further activated and deactivated by a magnetic switch that engages in the presence of a magnetic field. FIG. 12B shows an exemplary OBM image of porcine kidney tubules acquired ex-vivo with a non-miniaturized benchtop configuration according to this exemplary embodiment. For example, the field of view can be approximately 500 microns. FIG. 12C shows an exemplary OBM image of porcine kidney tubules acquired in-vivo with the device shown in FIG. 12A during a 1-week live animal implant study. The image in FIG. 12C was transmitted wirelessly from the exemplary battery-powered device approximately 1 hour after surgical implantation.

Exemplary Microscopy Modalities Images

FIGS. 13A-13C illustrate exemplary images acquired with certain exemplary microscope modalities utilizing the exemplary apparatus and method according to various exemplary embodiments of the present disclosure. For example, FIG. 13A shows an image of a superficial healthy human oral squamous epithelium with resolvable buccal cell nuclei 1301 acquired in-vivo and in-situ using an exemplary oblique back-illumination microscope. FIG. 13B shows an image of a cancerous human breast tissue acquired ex-vivo with an exemplary spectrally-encoded confocal microscope featuring cellular resolution. FIG. 13C shows a cross-sectional image of cancerous human prostate tissue ex-vivo using an exemplary optical coherence tomography microscope. These exemplary images illustrate cellular and tissue micro-architectural information that is possible to obtain using the exemplary apparatus and method according to various exemplary embodiments of the present disclosure.

Exemplary Implantable Oblique Back-Illumination Microscope Image Processing

Figure 14:
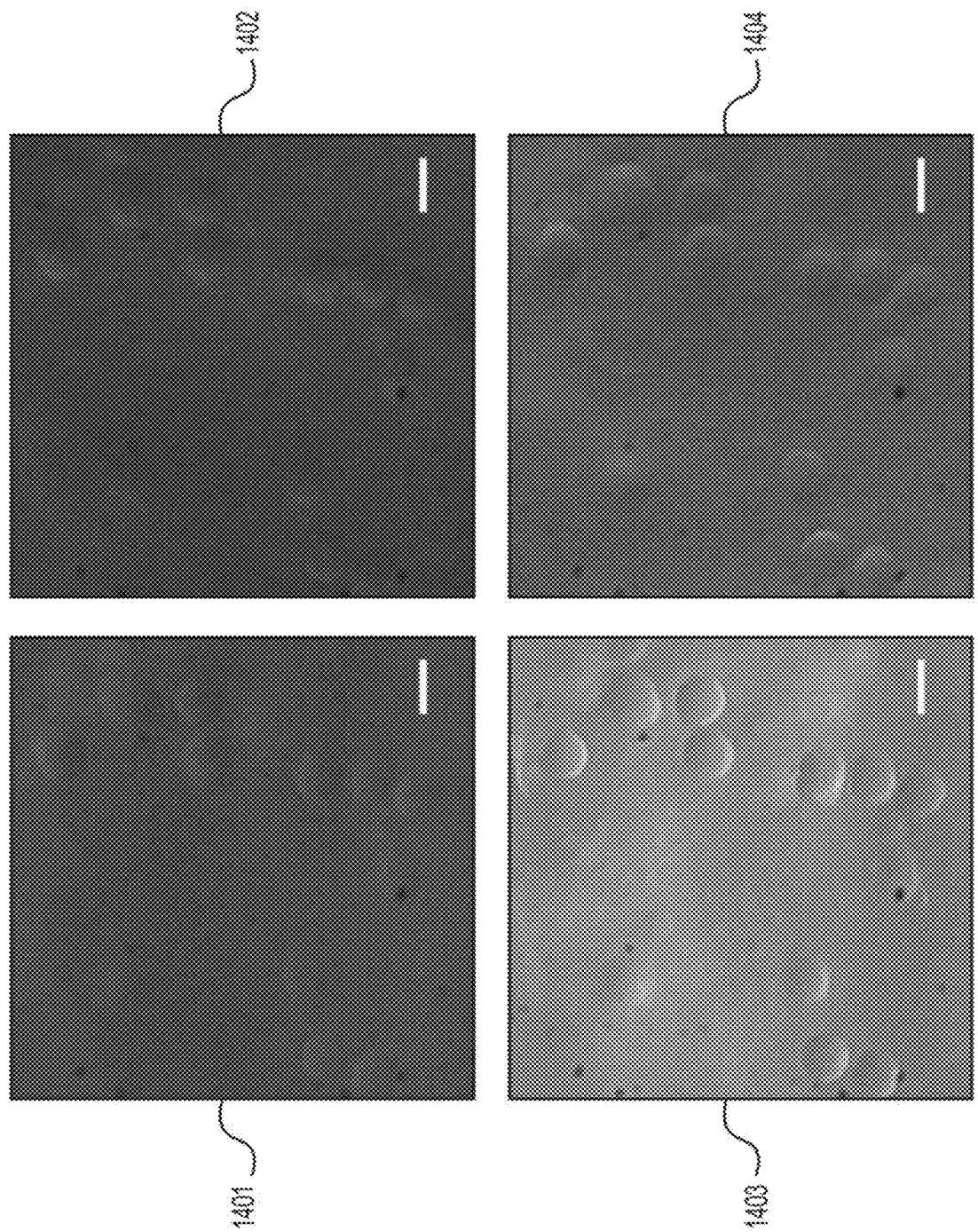
FIG. 14 is a set of illustrations obtained using a single camera exposure of a phantom sample of polystyrene beads in an aqueous medium according to an exemplary embodiment of the present disclosure.
Figure 15:
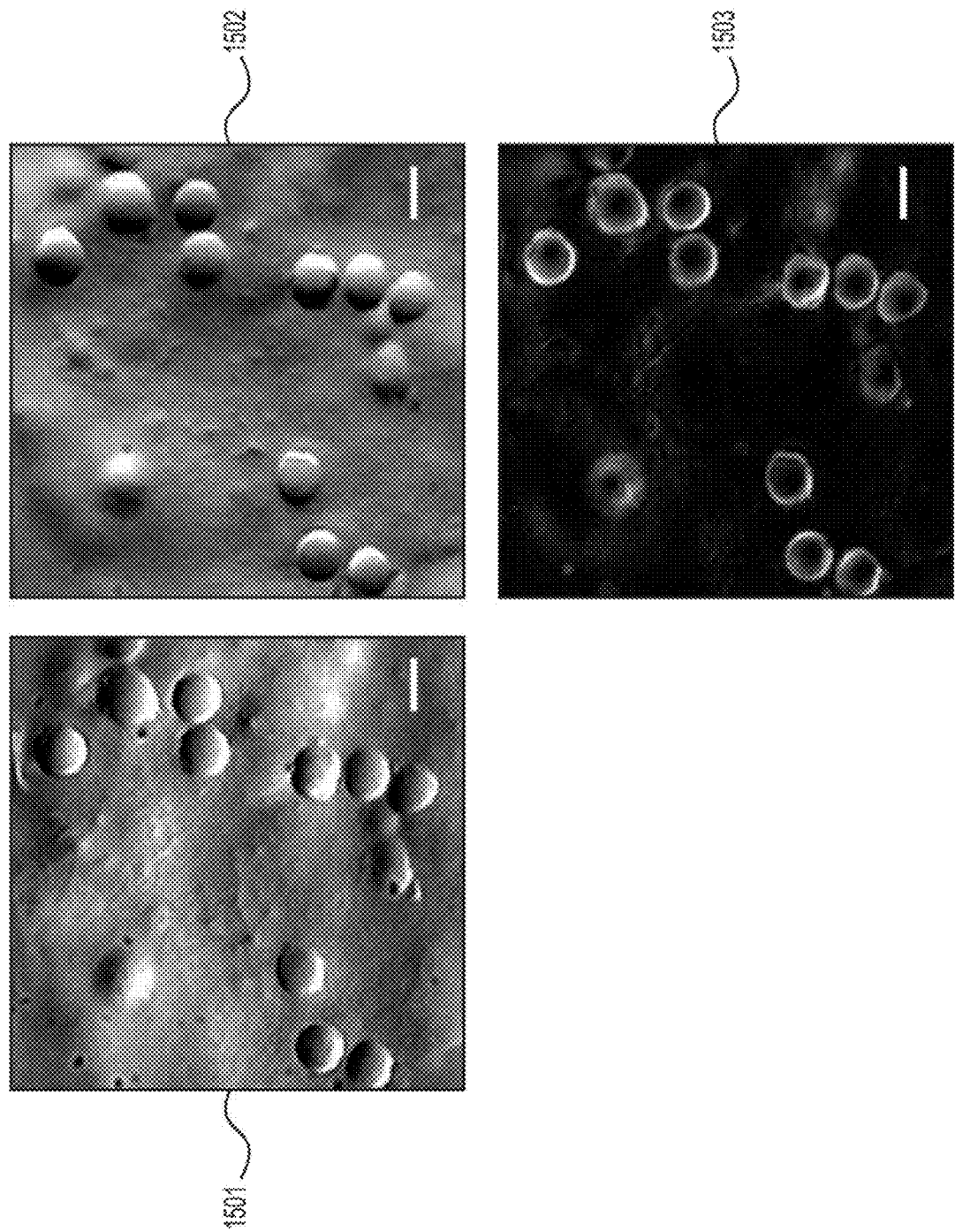
FIG. 15 is a set of illustrations in which pairs of images can be combined by subtracting an intensity-normalized version of the two exposures, leading to high-contrast phase gradient images according to an exemplary embodiment of the present disclosure.

In a further exemplary embodiment of the present disclosure, images obtained from disparately oblique illumination directions can be acquired by selectively activating a subset of the illumination sources in a sequence of exposures. FIG. 14 shows exemplary illustrations of an appearance of a single camera exposure of a phantom sample of polystyrene beads in an aqueous medium as each of four light-emitting diodes illuminates from above (see image 1401), from the left (see image 1402), from below (see image 1403), and from the right (see image 1404). The exemplary appearance of each bead is asymmetric due to the obliqueness of the illumination direction, though the low magnitude of the asymmetry can yield a low-contrast image in each individual exposure. Nonetheless, as illustrated in FIG. 15, pairs of exemplary images can be combined by subtracting an intensity-normalized version of the two exposures, leading to high-contrast phase gradient images. For example, in image 1501 of FIG. 15, the raw images 1401, 1403 shown in FIG. 14 can be combined to yield vertical-axis phase gradients. Further, in image 1502 of FIG. 15, the raw images 1402 and 1404 providing in FIG. 14 can be combined in a horizontal phase gradient image. Furthermore, the exemplary images shown in FIG. 14 can be combined in a single mathematical combination that approximates the direction-independent magnitude of the phase gradient (as shown in image 1503 of FIG. 15).

Exemplary Implantable SECM Microscope Image Processing

Figures 16A, 16B, 16C:
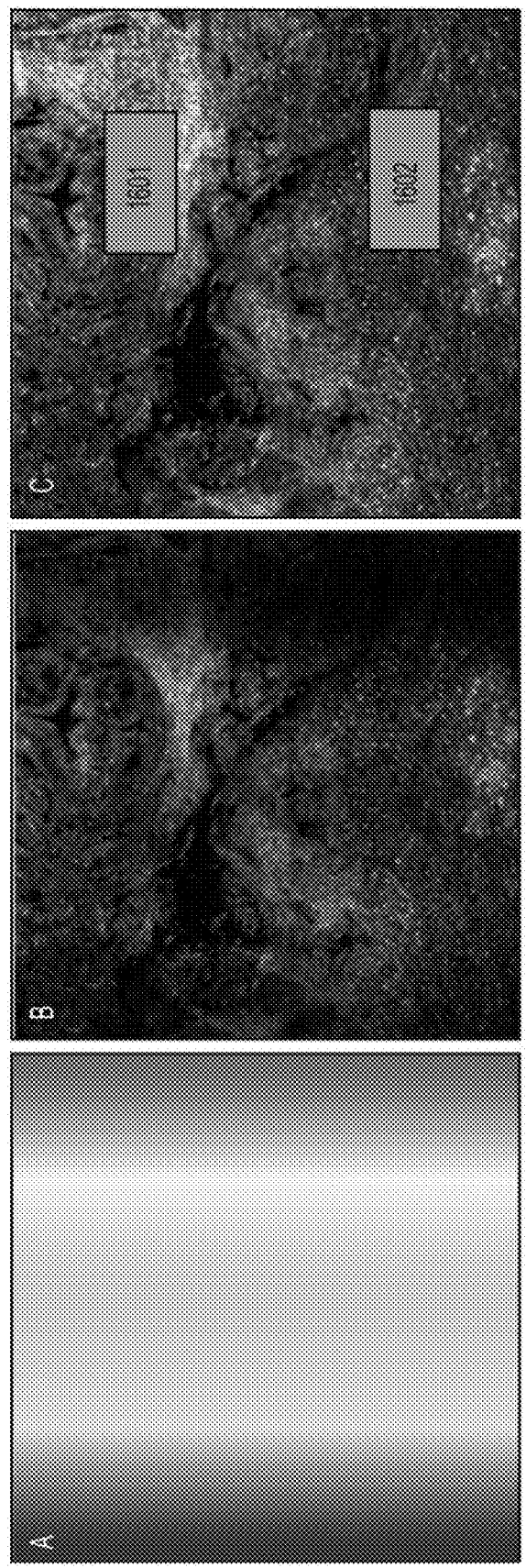
FIGS. 16A-16C are a set of illustrations which indicate exemplary image formation and exemplary image processing of an optical microscope modality that may be utilized in the exemplary systems according to various exemplary embodiments of the present disclosure.

FIG. 16A-16C illustrate exemplary image formation and image processing of the exemplary SECM implantable device shown in FIG. 9B. For example, FIG. 16A shows an exemplary broadband illumination pattern that has been laterally dispersed with a prism-grating-prisms (PGP). FIG. 16B shows an image of the product of confocal reflectance values from exemplary tissue with the spectrally-encoded illumination pattern. The spectrally-encoded reflected light is confocally gated by a slit aperture and collected with an area detector. The detected data can be coded, for example, with each row corresponding to a different vertical position of the tissue, and each column corresponding to a reflectance spectrum. By Fourier-transform processing each column spectrum, confocal reflectance values as a function of vertical and horizontal coordinate in the tissue can be obtained, as illustrated in FIG. 16C. The reconstructed image shows cancer cells 1601 invading healthy squamous mucosa 1602

Exemplary Implantable Device Utilization Workflow

Figure 17:
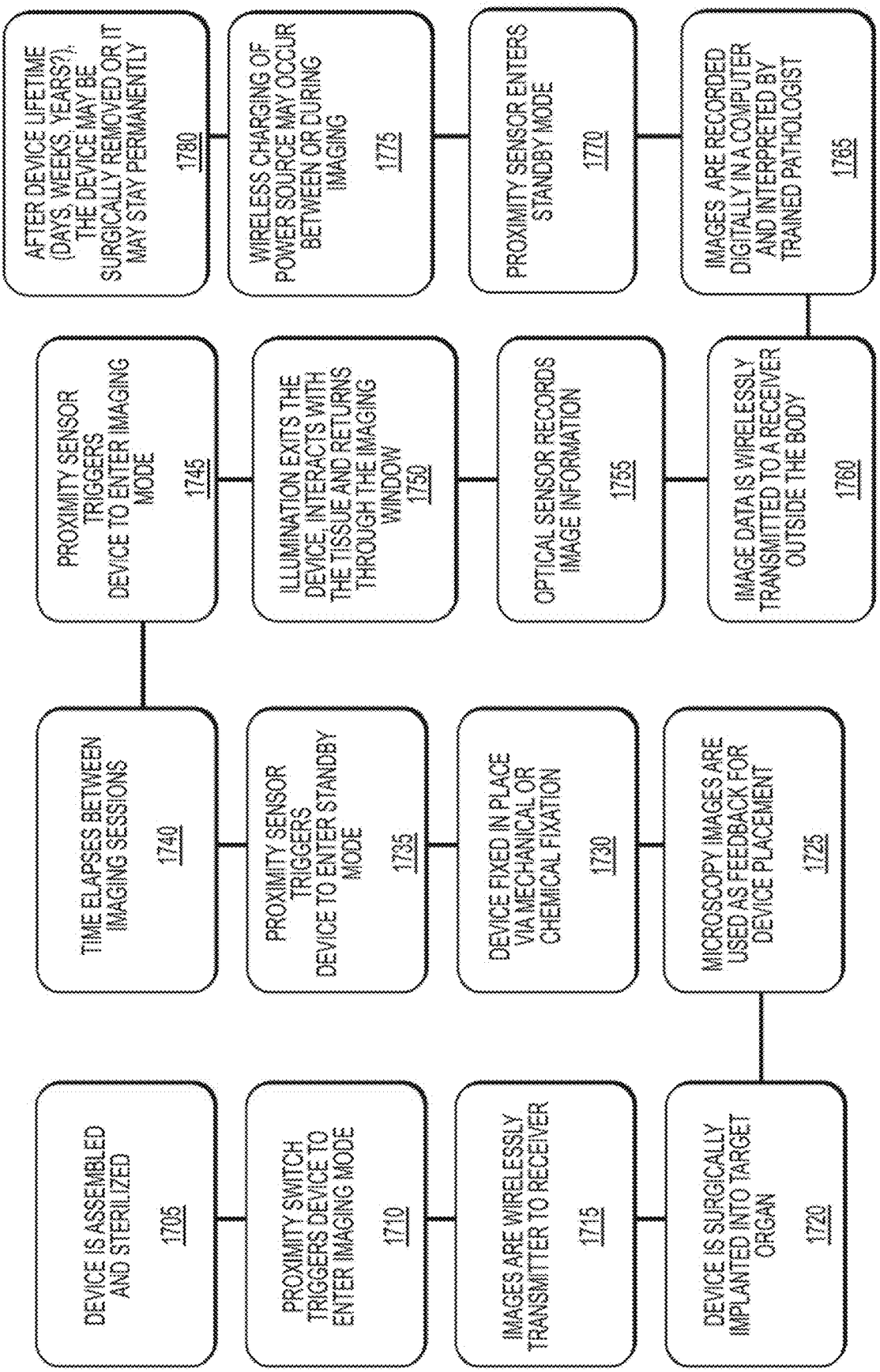
FIG. 17 is a flow diagram of a method according to an exemplary embodiment of the present disclosure.

FIG. 17 shows a flow diagram of a method according to an exemplary embodiment of the present disclosure. For example, as an initial matter, the device is first manufactured and sterilized for implantation (procedure 1705). Before implantation, the device is switched on using, e.g., a remote-actuated magnetic and/or proximity switch within the exemplary device (procedure 1710). The exemplary device then begins to actively transmit image data to an external receiving station, e.g., for display (procedure 1715). While the device is actively imaging, it can be surgically implanted into its desired target organ (procedure 1720), e.g., with transmitted microscopic images providing feedback for an optimization of the placement (procedure 1725). The exemplary device can then be stabilized and affixed to the tissue, either mechanically (such as, e.g., suturing) or chemically (such as, e.g., adhesion) (procedure 1730).

As shown in FIG. 17, with the device in place, it can then be switched off or be provided in a standby mode using the magnetic/proximity switch (procedure 1735). The exemplary device can then be dormant, e.g., drawing negligible electrical power as it awaits its next activation, with certain time elapsing (procedure 1740). When activated again using, e.g., the magnetic/proximity switch to enter an imaging mode (procedure 1745), the device powers on. The light source(s) can illuminate the sample, and the light interacts with the tissue, of which some portion may return through the imaging window (procedure 1750). The data corresponding to the information provided by the light can be recorded by the optical sensor or another device (procedure 1755). Again, this image data is transmitted wirelessly to an external display or storage station (procedure 1760), and can be interpreted on site by, e.g., a medical professional (procedure 1765) or re-transmitted through the Internet or other computer-accessible medium to a remote location for reading At the conclusion of this imaging session, the magnetic/proximity switch returns the device to its off or standby state (procedure 1770). During the time between this and any other image session, inductive, kinetic, or solar charging may be utilized to replenish the power level stored in the device's on-board battery or of another power source arrangement (procedure 1775). When the microscopic image monitoring of the organ tissue is no longer needed, the exemplary device may be removed surgically from the body and/or may remain implanted in an inert power-off state (procedure 1780).

The foregoing merely illustrates the principles of the disclosure. Various modifications and alterations to the described embodiments will be apparent to those skilled in the art in view of the teachings herein. Indeed, the arrangements, systems and methods according to the exemplary embodiments of the present disclosure can be used with and/or implement any OCT system, OFDI system, SD-OCT system or other imaging systems, and for example with those described in International Patent Application PCT/US2004/029148, filed Sep. 8, 2004 which published as International Patent Publication No. WO 2005/047813 on May 26, 2005, U.S. patent application Ser. No. 11/266,779, filed Nov. 2, 2005 which published as U.S. Patent Publication No. 2006/0093276 on May 4, 2006, and U.S. patent application Ser. No. 10/501,276, filed Jul. 9, 2004 which published as U.S. Patent Publication No. 2005/0018201 on Jan. 27, 2005, and U.S. Patent Publication No. 2002/0122246, published on May 9, 2002, the disclosures of which are incorporated by reference herein in their entireties. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly being incorporated herein in its entirety. All publications referenced above can be incorporated herein by reference in their entireties.

What is claimed is:

1. An apparatus, comprising:
   at least one light source which is configured to provide light to at least one portion of a biological structure to continuously illuminate the at least one portion of the biological structure,
   a grating, or prism to redirect light returned from the at least one portion of a biological structure at an angle towards at least one detector,
   the at least one detector being configured to detect microscopic images from the at least one portion continuously based on the light and provide data based on the detection,
   the microscopic images being at least one of optical sections or cross-sectional images through the at least one portion, wherein the combination of the at least one light source and the at least one detector produces the at least one of optical sections or cross-sectional images through the at least one portion by performing at least one of (i) an oblique back-illumination microscopy (OBM), (ii) a reflectance confocal microscopy (RCM), (iii) a spectrally encoded confocal microscopy (SECM), (iv) an optical coherence tomography (OCT), or (v) a full-field optical coherence microscopy (FF-OCM); and at least one implantable configuration which at least one of (i) is a particular surface of the apparatus, (ii) covers at least one portion of the surface, or (iii) extends from the surface, wherein the at least one implantable configuration prevents or reduces a movement of the apparatus from an exterior surface location of at least one anatomical body to provide for long-term, continuous monitoring, the apparatus being equal to 20 mm or less in diameter, and wherein the at least one anatomical body is an organ, and wherein the at least one portion of the biological structure is within the organ.

2. The apparatus according to claim 1, further comprising a transmitter which is coupled to the at least one detector, wherein the at least one detector is further configured to output additional data to be transmitted wirelessly to an external device that is outside the apparatus using the transmitter.

3. The apparatus according to claim 2, wherein the wireless transmission includes a radio frequency transmission.

4. The apparatus according to claim 2, wherein the fourth arrangement at least one of (i) includes a further light source which is configured to wirelessly transmit the data by modulating light emission therefrom, or (ii) configured to wirelessly transmit the data by modulating the first arrangement.

5. The apparatus according to claim 2, further comprising a transceiver configured to receive additional data from the external device, and wherein the processor is further configured to control at least one part of the at least one light source based on the additional data.

6. The apparatus according to claim 1, wherein, in operation, the apparatus is solely wirelessly communicating with an external device.

7. The apparatus according to claim 1, further comprising a processor which is configured to receive further data from the at least one detector which includes image data, and process the further data to generate information associated with microscopic data regarding the at least one portion.

8. The apparatus according to claim 1, further comprising at least one power source which is configured to power at least one of the at least one light source, the at least one detector, or a processor.

9. The apparatus according to claim 8, wherein the energy providing arrangement is recharged by at least one of the magnetic arrangement or a further induction arrangement.

10. The apparatus according to claim 8, further comprising a processor which is configured to control activation or deactivation of the at least one power source.

11. The apparatus according to claim 8, further comprising a power switch controlled by the processor so as to actuate the power switch, wherein the processor which detects a magnetic field strength from a source external from the biological structure, and wherein the processor utilizes information regarding the magnetic field strength to control the power switch.

12. The apparatus according to claim 1, wherein the at least one light source includes at least one of (i) at least two light-emitting diodes, (ii) at least one laser, or (iii) at least two super-luminescent diodes.

13. The apparatus according to claim 12, wherein the illuminating laser diodes provide the pulses that are passed through an oscillatory mechanism that is configured to reduce time-integrated laser speckle.

14. The apparatus according to claim 1, wherein the apparatus includes an optical element extending from the surface.

15. The apparatus of claim 1, wherein the microscopic images have a resolution of 20 µm or less.

16. The apparatus according to claim 1, wherein the at least one light source comprises a first light source and a second light source, each of which is configured to provide light to the at least one portion of the biological structure.

17. The apparatus according to claim 16, wherein the first light source and the second light source are incoherent light sources.

18. The apparatus according to claim 1, further comprising aspheric micro-optics which are configured to focus the light on the at least one detector to detect microscopic images from the at least one portion.

19. The apparatus according to claim 1, wherein the organ is at least one of a kidney, a liver, or a gastrointestinal tract.

20. A method, comprising:
providing, using at least one light source, light to at least one portion of a biological structure to continuously illuminate the at least one portion of the biological structure,
redirecting light returned from the at least one portion of a biological structure at an angle towards at least one detector using a grating, or prism;
continuously detecting, using at least one detector, microscopic images from the at least one portion based on the light,
the microscopic images being at least one of optical sections or cross-sectional images through the at least one portion, wherein detecting the microscopic images further comprises:
producing the at least one of optical sections or cross-sectional images through the at least one portion by performing at least one of:
oblique back-illumination microscopy (OBM);
reflectance confocal microscopy (RCM);
spectrally encoded confocal microscopy (SECM);
optical coherence tomography (OCT); or
full-field optical coherence microscopy (FF-OCM);
providing, by the at least one detector, data based on the detection; and
causing a prevention or a reduction of a movement of an implantable apparatus from an exterior surface location of at least one anatomical body using at least one configuration which at least one of (i) is a particular surface of the implantable apparatus, (ii) covers at least one portion of the surface, or (iii) extends from the surface to provide for long-term, continuous monitoring, the implantable apparatus being equal to 20 mm or less in diameter, and wherein the at least one anatomical body is an organ, and
wherein the at least one portion of the biological structure is within the organ.

21. The method of claim 20, wherein the microscopic images have a resolution of 20 µm or less.

22. The method of claim 20, wherein the at least one light source comprises a first light source and a second light source, each of which is configured to provide light to the at least one portion of the biological structure.

23. The method of claim 22, wherein the first light source and the second light source are incoherent light sources.

24. The method of claim 20, further comprising focusing the light on the at least one detector to detect microscopic images from the at least one portion using aspheric micro-optics.

25. The method of claim 20, wherein the organ is at least one of a kidney, a liver, or a gastrointestinal tract.

* * * * *